United States Patent

Martin et al.

[11] Patent Number: 4,868,202
[45] Date of Patent: Sep. 19, 1989

[54] PESTICIDAL COMPOSITIONS CONTAINING 3-PHENYLPYRROLE DERIVATIVES

[75] Inventors: Pierre Martin, Rheinfelden; Robert W. Lang, Pratteln, both of Switzerland

[73] Assignee: Ciba-Geigy Corporation, Ardsley, N.Y.

[21] Appl. No.: 136,687

[22] Filed: Dec. 22, 1987

Related U.S. Application Data

[60] Division of Ser. No. 77,072, Jul. 23, 1987, abandoned, which is a continuation of Ser. No. 787,223, Oct. 15, 1985, abandoned.

[30] Foreign Application Priority Data

Oct. 16, 1984 [CH] Switzerland ............ 4949/84

[51] Int. Cl.$^4$ .......... A01N 43/38; A01N 47/40; C07D 207/416; C07D 207/33
[52] U.S. Cl. .................. 514/423; 514/427; 548/561; 558/442; 560/170; 560/254; 562/430; 562/567; 568/812; 570/128; 570/144
[58] Field of Search ............ 548/561; 514/423, 427

[56] References Cited

U.S. PATENT DOCUMENTS 4,567,052 1/1986 Nyfeler ............ 548/561
4,709,053 11/1987 Martin ............ 548/561

Primary Examiner—Mark L. Berch
Attorney, Agent, or Firm—Edward McC. Roberts

[57] ABSTRACT

Novel 3-phenylpyrrole derivatives of the formula I

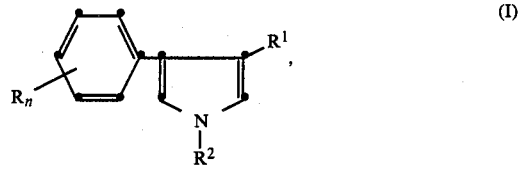

(I)

wherein $R^1$ is cyano, trifluoromethyl or $C_1$–$C_4$-alkoxycarbonyl, $R^2$ is vinyl or a group —$CH_2$—$CH_2$—X, in which X is chlorine or bromine, or is cyano, $C_1$–$C_4$-alkoxycarbonyl, phenylsulfonyl, 4-bromophenylsulfonyl or 4-methylphenylsulfonyl, R is halogen, $C_1$–$C_4$-alkyl or $C_1$–$C_4$-haloalkyl, and n is zero, one or two, have valuable microbicidal properties for controlling phytopathogenic plant pests, particularly phytopathogenic fungi.

11 Claims, No Drawings

PESTICIDAL COMPOSITIONS CONTAINING 3-PHENYLPYRROLE DERIVATIVES

This application is a division of application Ser. No. 077,072, filed July 23, 1987, now abandoned, which is a continuation of application Ser. No. 787,223, filed Oct. 15, 1985, now abandoned.

The present invention relates to novel 3-phenylpyrrole derivatives, to compositions containing them as active ingredients for controlling phytopathogenic microorganisms, to the use of these active ingredients, and also to processes and intermediates for producing the novel compounds.

The 3-phenylpyrrole derivatives according to the invention correspond to the formula I

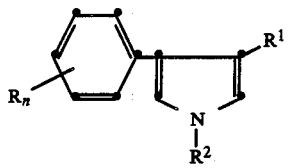

wherein $R^1$ is cyano, trifluoromethyl or $C_1$–$C_4$-alkoxycarbonyl, $R^2$ is vinyl or a group —$CH_2$—$CH_2$—X, in which X is chlorine, bromine, cyano, $C_1$–$C_4$-alkoxycarbonyl, phenylsulfonyl, 4-bromophenylsulfonyl or 4-methylphenylsulfonyl, R is halogen, $C_1$–$C_4$-alkyl or $C_1$–$C_4$-haloalkyl, and n is zero, one or two.

N-substituted pyrrole compounds have already been described in the literature for various application purposes. Compounds of this type are known from the G.B. Patent Specification No. 2,078,761 as stabilisers for plastics, or from the German Offenlegungsschrift No. 2,028,363 as polymerisation catalysts. N-Sulfenylated 3-phenylpyrrole compounds have recently been put forward as microbicides in for example the published European Patent Application No. EP-A 96,142.

Within the scope of the present invention, the term 'alkoxycarbonyl' denotes methoxycarbonyl, ethoxycarbonyl, i-propyloxycarbonyl and n-propyloxycarbonyl, as well as the four isomeric butyloxycarbonyl groups. Methoxy- or ethoxycarbonyl is preferred. The same definition and preference apply with respect to the term 'alkoxycarbonylethyl', which is represented by the symbol $R^2$. The preferred forms here are methoxycarbonylethyl and ethoxycarbonylethyl. Halogen is fluorine, chlorine, bromine or iodine, preferably chlorine. By alkyl is meant: methyl, ethyl, i-propyl and n-propyl, as well as the four isomeric butyl groups. Examples of haloalkyl are: fluoromethyl, difluoromethyl, trifluoromethyl, chloromethyl, trichloromethyl, 2,2,2-trifluoroethyl, 3,3,3-trichloroethyl, 2-chloroethyl, perfluoroethyl, 2-fluoroethyl and 1,1-dichloro-2,2,2-trifluoroethyl.

Preferred compounds of the formula I according to the invention are those wherein:
(a) the phenyl group is substituted in the 2- and 3-position by two chlorine atoms; or
(b) $R^1$ is cyano or trifluoromethyl; or
(c) $R^2$ is ethoxycarbonylethyl or 2-cyanoethyl.

More particularly preferred is a group of active substances of the formula I in which the phenyl group is substituted in the 2- and 3-position by chlorine atoms, $R^1$ is trifluoromethyl or cyano, and $R^2$ is ethoxycarbonylethyl or 2-cyanoethyl.

To be mentioned as preferred individual compounds are:
1-ethoxycarbonylethyl-3-(2,3-dichlorophenyl)-4-trifluoromethylpyrrole, and
1-ethoxycarbonylethyl-4-cyano-3-(2,3-dichlorophenyl)-pyrrole.

The novel compounds of the formula I are produced according to the invention by treating a formylglycine derivative of the formula II

wherein $R^2$ has the meaning defined under the formula I, in the presence of a condensation agent, with a phenylacetylene derivative of the formula III

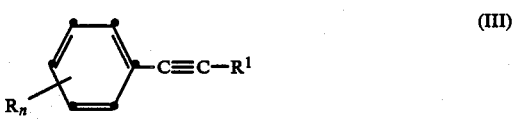

wherein $R^1$, R and n have the meanings defined under the formula I.

Suitable in a particular manner as a condensation agent is acetic anhydride. There can also be used however reagents such as dicyclohexylcarbodiimide, diisopropylcarbodiimide, trifluoroacetic anhydride or propionic anhydride. The process is performed either in an inert organic solvent, such as toluene, xylene or mesitylene, or without solvent in an excess of the condensation agent. The reaction temperature is in general the boiling temperature of the reaction mixture. Depending on the solvent, the reaction is performed at a temperature of between 90° and 150° C., preferably between 110° and 140° C.

The formylglycine derivatives of the formula II are novel, and have been developed and produced specially for the synthesis of the compounds of the formula I. They thus likewise form subject matter of the present invention.

These compounds are obtained, in a known manner, advantageously by formylation of a glycine ester of the formula

wherein $R^2$ has the meanings defined under the formula I, and T is $C_1$–$C_4$-alkyl, with formic acid, or by formylation of the corresponding glycine hydrochloride with an alkali formiate and subsequent saponification of the ester group.

The compounds of the formula III in which $R^1$ is cyano or $C_1$–$C_4$-alkoxycarbonyl are known, or they can be obtained, by processes analogous to known processes, by the addition of bromine and subsequent double elimination of hydrogen bromide from the corresponding derivatives of cinnamic acid.

Novel however are those compounds of the formula III in which $R^1$ is trifluoromethyl, and n is the number one or two. The synthesis of these compounds has been specially developed for the production of the compounds of the formula I. The novel compounds of the formula IIIa

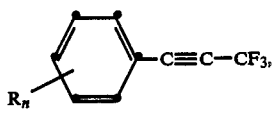

(IIIa)

wherein $R^1$ is trifluoromethyl, and n is the number one or two, and also the production process involving the use of these intermediates and further novel intermediates form therefore further subject matter of the present invention.

By a process according to the invention, there are obtained the 3-phenylpyrrole derivatives of the formula I, in which $R^1$ is trifluoromethyl, by cleaving off hydrogen chloride from a styrene derivative of the formula IV (IV)

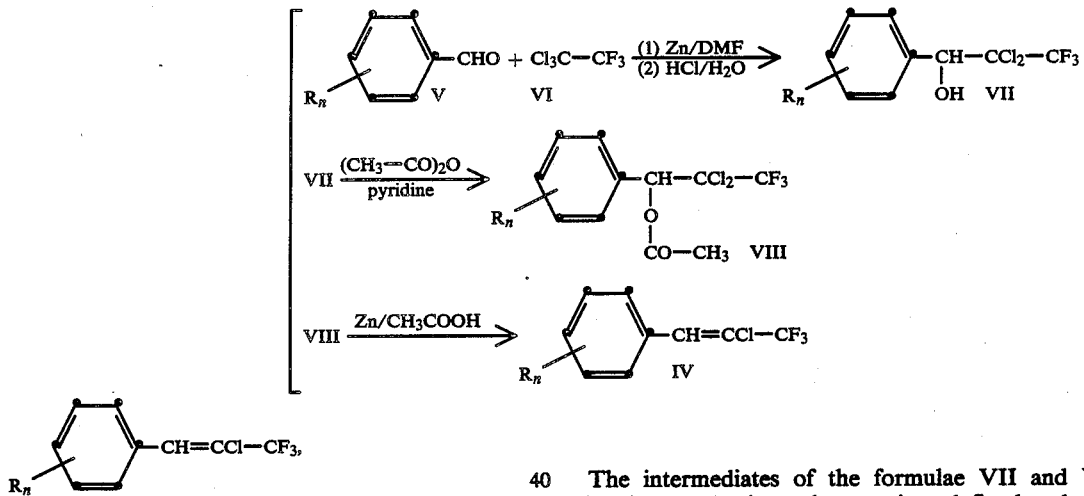

Scheme 1:

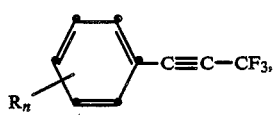

wherein R and n have the meanings defined under the formula I, in the presence of a base, and reacting the formed trifluoromethyl-phenylacetylene derivative of the formula IIIa

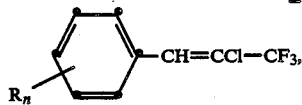

(IIIa)

wherein R and n have the meanings defined under the formula I, in the presence of a condensation agent, with a formylglycine derivative of the formula II

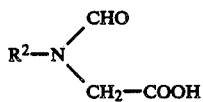

(II)

wherein $R^2$ has the meaning defined under the formula I.

The reaction conditions in the first step of the above process (IV→IIIa, cleavage of hydrogen chloride) correspond to those of customary procedures: there can thus be used a large number of bases, such as inorganic hydroxides, oxides, hydrogen carbonates or carbonates of alkali metals and alkaline-earth metals, or organic bases, such as tertiary amines, and the reaction can be performed in an inert polar, protic or aprotic solvent. Some typical reaction conditions for elimination reactions of this type are distinguished by the following reagent combinations: for example potassium hydroxide in methanol, ethanol or isopropanol; sodium methylate in methanol; potassium tert-butylate in tert-butanol; potassium tert-butylate in ethanol; sodium amide in liquid ammonia; potassium hydroxide in ethylene glycol dimethyl ether; sodium hydroxide in water; or sodium hydroxide in dimethyl sulfoxide. The reaction mixtures are advantageously heated or refluxed in carrying out the elimination reactions. The second reaction step is performed according to the reaction conditions for the reaction (II+III→I) already described in the foregoing.

The starting products of the formula IV are likewise novel. They can be obtained for example by reactions according to the following reaction scheme 1:

The intermediates of the formulae VII and VIII wherein R and n have the meanings defined under the formula I, which stages are passed through according to scheme 1, have not hitherto been described in the literature. They likewise form subject matter of the present invention.

The novel pyrrole derivatives of the formula I according to the invention constitute a valuable enlargement of the prior art, for it has been established that the novel pyrroles of the formula I surprisingly exhibit a microbicidal spectrum against phytopathogenic fungi and bacteria which is very favourable for agricultural requirements. They not only can be used in arable farming or in similar fields of application for controlling harmful microorganisms on cultivated plants, but can be additionally used, in the protection of stocks, for preserving perishable goods. Compounds of the formula I have very advantageous curative, systemic and in particular preventive properties, and can be used for the protection of numerous, especially arable, crops. The microorganisms occurring on plants or on parts of plants (fruit, blossom, foliage, stalks, tubers or roots) of various cultivated crops can be inhibited or destroyed with the active substances of the formula I, and also parts of plants subsequently growing remain preserved from such microorganisms.

The active substances are effective for example against the phytopathogenic fungi belonging to the following classes: Ascomycetes, for example Erysiphe, Sclerotinia, Fusarium, Monilinia and Helminthosporium; Basidiomycetes, for example Puccinia, Tilletia and Rhizoctonia; and also against the Oomycetes belonging to the Phycomycetes class, such as Phytophthora. As plant protective agents, the compounds of the formula I can be applied with a particularly high degree of success against important harmful fungi from the Fungi imperfecti family, for example against Cercospora or Piricularia, and especially against Botrytis. Botrytis spp. (*B. cinera, B. allii*) constitute with botrytis disease on grapevines, strawberries, apples, onions and other fruit and vegetable varieties a significant economic loss factor. Furthermore, some compounds of the formula I can be successfully used for protecting perishable goods of vegetable or animal origin. They combat mould fungi, such as Penicillium, Aspergillus, Rhizopus, Fusarium, Helminthosporium, Nigrospora and Alternaria, as well as bacteria, such as butyric acid bacteria, and yeasts, such as Candida.

As plant protective agents, the compounds of the formula I exhibit, for practical application in agriculture, a very favourable spectrum of activity for protecting cultivated plants, without disadvantageously affecting these by undesirable side effects.

The compounds can also be used as dressing agents for the treatment of seed (fruits, tubers or grain), and of plant cuttings to protect them from fungus infections, and also against phytopathogenic fungi occurring in the soil.

The invention thus relates also to microbicidal compositions, and to the use of the compounds of the formula I for controlling phytopathogenic microorganisms, especially fungi which damage plants, and for preventing an infestation on plants and on provisions of vegetable or animal origin.

In addition, the present invention embraces also the production of (agro)chemical compositions, whereby the active ingredient is intimately mixed with one or more substances or groups of substances described herein. Also included is a process for treating plants or stored provisions, which process comprises the application of the compounds of the formula I, or of the novel compositions, to the plants or parts of plants, or to the locus or the substrate thereof.

Within the scope of this invention, target crops for plant protection are for example the following varieties of plants: cereals (wheat, barley, rye, oats, rice, sorghum and related cereals); beet (sugar beet and fodder beet); pomaceous fruit, stone fruit and soft fruit (apples, pears, plums, peaches, almonds, cherries, strawberries, raspberries and blackberries); legumes (beans, lentils, peas and soya-beans); oil plants (rape, mustard, poppy, olives, sunflowers, coco, castor-oil plants, cocoa and groundnuts); Curcurbitacea (pumpkins, cucumbers and melons); fibre plants (cotton, flax, hemp and jute); citrus fruits (oranges, lemons, grapefruit and mandarins); varieties of vegetables (spinach, lettuce, asparagus, varieties of cabbage, carrots, onions, tomatoes, potatoes and paprika); laurel plants (avocada, cinnamon and camphor); or plants such as maize, tobacco, nuts, coffee, sugar cane, tea, grapevines, hops, bananas and natural rubber plants; and also ornamental plants (composites).

As protective agents for stored products, the compounds of the formula I are used either in an unmodified form or preferably together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, scattering, brushing or pouring, and likewise the type of composition, are selected to suit the objectives to be achieved and the prevailing conditions. Favourable applied amounts are in general 0.01 to at most 2 kg of active ingredient per 100 kg of substrate to be protected; the amounts depend however quite considerably on the nature (extent of surface area, consistency, and moisture content) of the substrate and on environmental influences thereon.

Within the scope of the present invention, stored stocks and provisions are vegetable and/or animal natural materials and products from further processing, for example the plants which are listed in the following and which have been taken out from the natural life cycle, and parts of these plants (stalks, leaves, tubers, seeds, fruits and grains), the materials being in the freshly harvested conditions or in the form resulting from further processing (pre-dried, moistened, crushed, ground or roasted). The following productive materials may be given as examples, which however have no limiting character with respect to the scope of this invention: cereals (such as wheat, barley, rye, oats, rice, sorghum and related cereals); beet (such as carrots, sugar beet and fodder beet); pomaceous fruit, stone fruit and soft fruit (such as apples, pears, plums, almonds and cherries); legumes (such as beans, lentils, peas and soya-bean); oil plants (such as rape, mustard, poppy, sunflowers, coco, castor-oil plants, cocoa and groundnuts); Cucurbitacea (such as pumpkins, cucumbers and melons); fibre plants (such as cotton, flax, hemp, jute and nettles); citrus fruits; varieties of vegetables (such as varieties of cabbage, onions, tomatoes, potatoes and paprika); laurel plants (such as avocada, cinnamon and camphor); or plants such as maize, tobacco, nuts, coffee, sugar cane, tea, chestnuts, hops, bananas, grass and hay.

Natural products of animal origin which may be mentioned are in particular dried processed meat and fish products, such as dried meat, dried fish, meat concentrates, bone meal, fish meal and dried animal feed.

By treatment with compounds of the formula I, the treated stored products are lastingly protected against infestation by mould fungi and other undesirable microorganisms. Consequently, the formation of toxic and in part carcinogenic mould fungi or metabolic products thereof, such as aflatoxines and ochratoxines, is prevented, the material is kept from decomposing, and the quality thereof is maintained high for a prolonged period of time. The process according to the invention can be applied to all dry and moist provisions and stored goods which are susceptible to microorganisms, such as yeasts, bacteria and especially mould fungi.

A preferred process for applying the active substance comprises spraying or wetting the substrate with a liquid preparation, or mixing the substrate with a solid preparation of the active substance. The described conservation process forms a part of the present invention.

Active substances of the formula I are customarily used in the form of compositions, and can be applied, simultaneously or successively, with further active substances to the area, plants or substrate to be treated. These further active substances can be fertilisers, trace-element agents or other preparations influencing plant growth. They can however also be selective herbicides, insecticides, fungicides, bactericides, nematicides or molluscicides, or mixtures of several of these preparations, optionally together with carriers commonly used in formulation practice, tensides or other additives facilitating application.

Suitable carriers and additives can be solid or liquid and they correspond to the substances customarily employed in formulation practice, for example: natural or regenerated mineral substances, solvents, dispersing agents, wetting agents, adhesives, thickeners, binders or fertilisers.

A preferred method of applying an active substance of the formula I, or an (agro)chemical composition containing at least one of these active substances, is application to the foliage (leaf application). The number of applications and the amounts applied are governed by the extent of infestation with respect to the pathogen (fungus genus) concerned. The active substances of the formula I can however be fed into the plant through the soil and then by way of the root system (systemic action), this being achieved by the locus of the plant being soaked with a liquid preparation, or by the substances being introduced in solid form into the soil, for example in the form of a granulate (soil application). The compounds of the formula I can also be applied to the seed grains (coating), the grains being for this purpose either soaked with a liquid preparation of the active substance or coated with a solid preparation. Further forms of application are possible in special cases, for example the specific treatment of the stalks or buds of the plants.

The compounds of the formula I are used either in an unmodified form or preferably together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions. Favourable applied amounts are in general between 50 g and 5 kg of active substance (AS) per hectare, preferably between 100 g and 2 kg of AS per hectare, and in particular between 200 g and 600 g of AS per hectare.

The formulations, that is to say, the compositions or preparations containing the active substance of the formula I and optionally a solid or liquid additive, are produced in a known manner, for example by the intimate mixing and/or grinding of the active ingredient with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl-or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil, sunflower oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is possible to also add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues, for example cork powder or sawdust.

Particularly advantageous additives facilitating application and rendering possible a marked reduction in the amount of active substance applied are moreover natural (animal or vegetable) or synthetic phospholipides from the class comprising the cephalins and lecithins, for example: phosphatidylethanolamine, phosphatidylserine, phosphatidylcholine, sphingomyelin, phosphatidylinosite phosphatidyl glycerol, lysolecithin, plasmalogenes or cardiolipin, which can be obtained for example from animal or plant cells, especially from the brain, heart, liver, egg yokes or soya beans. Applicable commercial mixtures are for example phosphatidylcholine mixtures. Synthetic phospholipides are for example dioctanoylphosphatidylcholine and dipalmitoylphosphatidylcholine.

Depending on the nature of the active ingredient of the formula I to be formulated, suitable surface-active compounds are nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic surface-active compounds.

Soaps which are applicable are for example the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-laurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanol, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)-ethylammonium bromide. In the field covering stored provisions, the additives which are preferred are those that are safe for human and animal foodstuffs.

The tensides customarily used in formulation practice are described, inter alia, in the following publications:
"Mc Cutcheon's Detergents and Emulsifiers Annual" MC Publishing Corp., Ridgewood, N.J., 1981;
H. Stache, "Tensid-Taschenbuch" (Tenside Handbook), 2nd Edition, C. Hanser Verlag, Munich/Vienna, 1981, and
M. and J. Ash, "Encyclopedia of Surfactants", Vol. I–III, Chemical Publishing Co., New York, 1980–1981.

The agrochemical preparations contain as a rule 0.1 to 99%, particularly 0.1 to 95%, of active ingredient of the formula I, 99.9 to 1%, especially 99.8 to 5%, of a solid or liquid additive, and 0 to 25%, in particular 0.1 to 25%, of a tenside.

Whereas commercial products are preferably in the form of concentrated compositions, the preparations employed by the end-user are as a rule diluted.

The compositions can contain further additives, such as stabilisers, antifoaming agents, viscosity regulators, binders and adhesives, as well as fertilisers or other active ingredients for obtaining special effects.

(Agro)chemical compositions of the types described herein likewise form part of the present invention.

The following Examples serve to further illustrate the invention without limiting the scope thereof. Percentage values and 'parts' relate to weight. There are also used the following symbols: h=hour; RT=room temperature; abs.=absolutely anhydrous; DMF=dimethylformamide; and pressure values are in millibar (mb) or bar (b).

PRODUCTION EXAMPLES

Example P1:

N-Ethoxycarbonylethyl-N-formylglycine 115.5 g of N-ethoxycarbonylethyl-N-formylglycine ethyl ester are dissolved in 150 ml of ethanol, and the solution is cooled to 0° C. To it is then added dropwise a mixture of 28.0 g of potassium hydroxide, 60 ml of water and 120 ml of ethanol. The reaction mixture is stirred for 18 h at RT, and is subsequently concentrated by evaporation under reduced pressure. After the addition of a small amount of water, the mixture is acidified with concentrated hydrochloric acid to pH 1. By extraction with chloroform, drying, and concentration of the organic phase by evaporation, there is obtained N-ethoxycarbonylethyl-N-formylglycine in the form of a yellowish oil (compound No. 1.3).

Example P2:

N-(2-Cyanoethyl)-N-formylglycine

A mixture of 21.0 g of N-(2-cyanoethyl)-glycine ethyl ester and 18.3 g of formic acid is refluxed for 2 h. After concentration of this mixture under reduced pressure, the residue is taken up in 50 ml of ethanol, and cooled to 0° C.; there is then added dropwise a solution of 25.5 g of potassium hydroxide and 40 ml of water in 80 ml of ethanol. After the reaction solution has warmed up to room temperature, the solvent is evaporated off, and the residue is acidified to pH 1 with conc. hydrochloric acid. The mixture is saturated with sodium chloride and subsequently extracted with ethyl acetate. The combined organic extracts are concentrated by evaporation to thus obtain N-(2-cyanoethyl)-N-formylglycine, m.p. 112°–114° C. (compound No. 1.1).

Example P3:

(2-Chloro-3,3,3-trifluoropropen-1-yl)-2,3-dichlorobenzene (a)
(2,2-Dichloro-3,3,3-trifluoro-1-hydroxypropyl)-2,3-dichlorobenzene A suspension of 35.0 g of 2,3-dichlorobenzaldehyde, 41.2 g of 1,1,1-trichloro-2,2,2-trifluoroethane and 16.4 g of zinc powder in 360 ml of DMF is stirred for 66 h at RT, and subsequently taken up in a mixture of 600 ml of 10% hydrochloric acid and 600 g of ice. By extraction with ether, drying, and concentration of the organic extracts by evaporation, there is obtained (2,2-dichloro-3,3,3-trifluoro-1-hydroxypropyl)-2,3-dichlorobenzene in the form of a yellow oil (compound No. 5.10).

(b)
(1-Acetoxy-2,2-dichloro-3,3,3-trifluoropropyl)-2,3-dichlorobenzene 33.0 g of pyridine are added to a mixture of 57.0 g of (2,2-dichloro-3,3,3-trifluoro-1-hydropropyl)-2,3-dichlorobenzene and 39.1 g of acetic anhydride, and the whole is stirred for 4 h at RT. The mixture is poured into ice-water, acidified with 10% hydrochloric acid, extracted with ether and dried; the ethereal extracts are subsequently concentrated by evaporation to thus obtain (1-acetoxy-2,2-dichloro-3,3,3-trifluoropropyl)-2,3-dichlorobenzene, m.p. 92°–95° C. from ethanol (compound No. 6.10).

(c) A solution of 59.0 g of (1-acetoxy-2,2-dichloro-3,3,3-trifluoropropyl)-2,3-dichlorobenzene in 350 ml of acetic acid is heated to 40° C., and 13.0 g of zinc powder are added portionwise. To effect completion of the reaction, the reaction mixture is heated at 90° C. for 3 hours. In further processing, the reaction mixture is taken up in ice-water, and extracted with ether. The combined organic phases are washed with water, sodium hydrogen carbonate solution and sodium chloride solution; they are then dried over magnesium sulfate, and concentrated by evaporation to thus obtain (2- chloro-3,3,3-trifluoropropen-1-yl)-2,3-dichlorobenzene in the form of yellow oil (compound No. 4.10).

Example P4:

1-Ethoxycarbonylethyl-3-(2,3-dichlorophenyl)-4-trifluoromethylpyrrole (a) 2,3-Dichloro-(3,3,3-trifluoropropyn-1-yl)-benzene To a solution of 31.7 g of (2-chloro-3,3,3-trifluoropropen-1-yl)-2,3-dichlorobenzene in 50 ml of tert-butanol, there is added dropwise at RT a solution of 14.1 g of potassium tert-butylate in 750 ml of tert-butanol in such a manner that the temperature of the reaction solution does not exceed 30° C. After continued stirring at RT for 18 h, the mixture is taken up in ice-water and extracted with ether. The organic phases are combined, washed with water and sodium chloride solution, and concentrated by evaporation. There is thus obtained, after distillation in vacuo, 2,3-dichloro-(3,3,3-trifluoropropyn-1-yl)-benzene in the form of colourless oil, b.p. 92°-98° C. at 22 mb (compound No. 2.27).

(b) 23.9 g of 2,3-dichloro-(3,3,3-trifluoropropyn-1-yl)-benzene and 20.3 g of N-ethoxycarbonylethyl-N-formylglycine are dissolved in 100 ml of acetic anhydride, and the solution is refluxed for 24 h. The mixture is concentrated by evaporation under reduced pressure; the residue is subsequently taken up in toluene, and purified by chromatography through silica gel. The solvent is evaporated off, and from the eluate is thus obtained 1-ethoxycarbonylethyl-3-(2,3-dichlorophenyl)-4-trifluoromethylpyrrole in the form of a colourless oil (compound No. 3.117).

Example P5:

4-Ethoxycarbonyl-1-(2-cyanoethyl)-3-phenylpyrrole 17.4 g of phenylacetylenecarboxylic acid ethyl ester and 15.6 g of N-(2-cyanoethyl)-N-formylglycine are dissolved in 100 ml of acetic anhydride, and the solution is refluxed for 24 h. The mixture is concentrated by evaporation under reduced pressure; the residue is then taken up in toluene, and purified by chromatography through silica gel. The solvent is evaporated off, and from the eluate is obtained 4-ethoxycarbonyl-1-(2-cyanoethyl)-3-phenylpyrrole in the form of a yellow oil (compound No. 3.3).

Example P6:

1-(2-Cyanoethyl)-3-(2,3-dichlorophenyl)-4-trifluoromethylpyrrole 23.9 g of 2,3-dichloro-(3,3,3-trifluoropropyn-1-yl)-benzene and 15.6 g of N-(2-cyanoethyl)-N-formylglycine are dissolved in 100 ml of acetic anhydride, and the solution is refluxed for 24 h. The mixture is concentrated by evaporation under reduced pressure; the residue is then taken up in toluene, and purified by chromatography through silica gel. The solvent is evaporated off, and from the eluate is obtained 1-(2-cyanoethyl)-3-(2,3-dichlorophenyl)-4-trifluoromethylpyrrole, m.p. 83°-85° C. from ether/hexane (compound No. 3.28).

There are obtained in an analogous manner the intermediates and final products listed in the following Tables.

TABLE 1

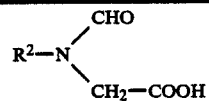

$$R^2-N\diagdown^{CHO}_{CH_2-COOH}$$

| Comp. No. | $R^2$ |
|---|---|
| 1.1 | $-CH_2-CH_2-CN$ |
| 1.2 | $-CH_2-CH_2-COOCH_3$ |
| 1.3 | $-CH_2-CH_2-COOC_2H_5$ |
| 1.4 | $-CH_2-CH_2-COOC_3H_7-i$ |
| 1.5 | $-CH_2-CH_2-COOC_3H_7-n$ |
| 1.6 | $-CH_2-CH_2-COOC_4H_9-n$ |
| 1.7 | $-CH=CH_2$ |
| 1.8 | $-CH_2-CH_2-Cl$ |
| 1.9 | $-CH_2-CH_2-SO_2-C_6H_4-CH_3$ |
| 1.10 | $-CH_2-CH_2-SO_2-C_6H_4-Br$ |
| 1.11 | $-CH_2-CH_2-SO_2-C_6H_5$ |
| 1.12 | $-CH_2-CH_2-Br$ |

TABLE 2

$$E-C\equiv C-R^1$$

| Comp.No | E | $R^1$ |
|---|---|---|
| 2.1 | $C_6H_5-$ | $CF_3$ |
| 2.2 | $C_6H_5$ | $COOCH_3$ |
| 2.3 | $C_6H_5$ | $COOC_2H_5$ |
| 2.4 | $C_6H_5$ | $CN$ |
| 2.5 | $2\text{-}Cl-C_6H_4-$ | $CF_3$ |
| 2.6 | $2\text{-}Cl-C_6H_4-$ | $COOC_2H_5$ |
| 2.7 | $2\text{-}Cl-C_6H_4-$ | $CN$ |
| 2.8 | $2\text{-}Cl-C_6H_4-$ | $COOC_3H_7-i$ |
| 2.9 | $3\text{-}Cl-C_6H_4-$ | $CF_3$ |
| 2.10 | $3\text{-}Cl-C_6H_4-$ | $CN$ |
| 2.11 | $3\text{-}Cl-C_6H_4-$ | $COOC_2H_5$ |
| 2.12 | $3\text{-}Cl-C_6H_4-$ | $COOC_4H_9-n$ |
| 2.13 | $2\text{-}CF_3-C_6H_4-$ | $COOCH_3$ |
| 2.14 | $2\text{-}CF_3-C_6H_4-$ | $COOC_2H_5$ |
| 2.15 | $2\text{-}CF_3-C_6H_4-$ | $CF_3$ |
| 2.16 | $2\text{-}CF_3-C_6H_4-$ | $CN$ |
| 2.17 | $4\text{-}Cl-C_6H_4-$ | $COOCH_3$ |
| 2.18 | $4\text{-}Cl-C_6H_4-$ | $CF_3$ |
| 2.19 | $4\text{-}Cl-C_6H_4-$ | $CN$ |
| 2.20 | $2\text{-}CF_3\text{-}4\text{-}Cl-C_6H_3-$ | $CN$ |
| 2.21 | $2\text{-}CF_3\text{-}4\text{-}Cl-C_6H_3-$ | $CF_3$ |
| 2.22 | $2\text{-}CF_3\text{-}4\text{-}Cl-C_6H_3-$ | $COOCH_3$ |
| 2.23 | $2\text{-}Cl\text{-}4\text{-}Cl-C_6H_3-$ | $CN$ |
| 2.24 | $2\text{-}Cl\text{-}4\text{-}Cl-C_6H_3-$ | $CF_3$ |
| 2.25 | $2\text{-}Cl\text{-}4\text{-}Cl-C_6H_3-$ | $COOC_2H_5$ |
| 2.26 | $2\text{-}Cl\text{-}3\text{-}Cl-C_6H_3-$ | $CN$ |
| 2.27 | $2\text{-}Cl\text{-}3\text{-}Cl-C_6H_3-$ | $CF_3$ |
| 2.28 | $2\text{-}Cl\text{-}3\text{-}Cl-C_6H_3-$ | $COOCH_3$ |
| 2.29 | $2\text{-}Cl\text{-}3\text{-}Cl-C_6H_3-$ | $COOC_2H_5$ |
| 2.30 | $2\text{-}Cl\text{-}3\text{-}Cl-C_6H_3-$ | $COOC_3H_7-i$ |
| 2.31 | $2\text{-}Cl\text{-}3\text{-}Cl-C_6H_3-$ | $COOC_3H_7-n$ |
| 2.32 | $2\text{-}Cl\text{-}3\text{-}Cl-C_6H_3-$ | $COOC_4H_9-n$ |
| 2.33 | $2\text{-}Cl\text{-}3\text{-}Cl-C_6H_3-$ | $COOC_4H_9-s$ |
| 2.34 | $2\text{-}Cl\text{-}3\text{-}Cl-C_6H_3-$ | $COOC_4H_9-i$ |
| 2.35 | $2\text{-}Cl\text{-}3\text{-}Cl-C_6H_3-$ | $CF_3$ |
| 2.36 | $2\text{-}Cl\text{-}4\text{-}CF_3-C_6H_3-$ | $CN$ |
| 2.37 | $2\text{-}Cl\text{-}4\text{-}CF_3-C_6H_3-$ | $COOCH_3$ |
| 2.38 | $2\text{-}Cl\text{-}4\ C_6H_3-$ | $COOC_2H_5$ |
| 2.39 | $4\text{-}CH_3-C_6H_4-$ | $CF_3$ |
| 2.40 | $4\text{-}CH_3-C_6H_4-$ | $CN$ |
| 2.41 | $4\text{-}CH_3-C_6H_4-$ | $COOCH_3$ |
| 2.42 | $2\text{-}F-C_6H_4-$ | $CF_3$ |
| 2.43 | $2\text{-}F-C_6H_4-$ | $CN$ |
| 2.44 | $2\text{-}F-C_6H_4-$ | $COOCH_3$ |

TABLE 3

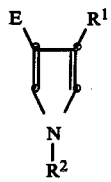

| Comp. No. | E | $R^1$ | $R^2$ |
|---|---|---|---|
| 3.1 | $C_6H_5$— | $CF_3$ | —$CH_2$—$CH_2$—CN |
| 3.2 | $C_6H_5$— | $COOCH_3$ | —$CH_2$—$CH_2$—CN |
| 3.3 | $C_6H_5$— | $COOC_2H_5$ | —$CH_2$—$CH_2$—CN |
| 3.4 | $C_6H_5$— | CN | —$CH_2$—$CH_2$—CN |
| 3.5 | 2-Cl—$C_6H_4$— | $CF_3$ | —$CH_2$—$CH_2$—CN |
| 3.6 | 2-Cl—$C_6H_4$— | $COOC_2H_5$ | —$CH_2$—$CH_2$—CN |
| 3.7 | 2-Cl—$C_6H_4$— | CN | —$CH_2$—$CH_2$—CN |
| 3.8 | 2-Cl—$C_6H_4$— | $COOCH_3$ | —$CH_2$—$CH_2$—CN |
| 3.9 | 2-Cl—$C_6H_4$— | $COOC_3H_7$—i | —$CH_2$—$CH_2$—CN |
| 3.10 | 3-Cl—$C_6H_4$— | $CF_3$ | —$CH_2$—$CH_2$—CN |
| 3.11 | 3-Cl—$C_6H_4$— | CN | —$CH_2$—$CH_2$—CN |
| 3.12 | 3-Cl—$C_6H_4$— | $COOC_2H_5$ | —$CH_2$—$CH_2$—CN |
| 3.13 | 3-Cl—$C_6H_4$— | $COOC_4H_9$—n | —$CH_2$—$CH_2$—CN |
| 3.14 | 2-F.$C_6H_4$— | $CF_3$ | —$CH_2$—$CH_2$—CN |
| 3.15 | 2-F—$C_6H_4$— | CN | —$CH_2$—$CH_2$—CN |
| 3.16 | 2-F—$C_6H_4$— | $COOCH_3$ | —$CH_2$—$CH_2$—CN |
| 3.17 | 2-$CF_3$—$C_6H_4$— | $COOC_2H_5$ | —$CH_2$—$CH_2$—CN |
| 3.18 | 2-$CF_3$—$C_6H_4$— | $COOCH_3$ | —$CH_2$—$CH_2$—CN |
| 3.19 | 2-$CF_3$—$C_6H_4$— | $CF_3$ | —$CH_2$—$CH_2$—CN |
| 3.20 | 2-$CF_3$—$C_6H_4$— | CN | —$CH_2$—$CH_2$—CN |
| 3.21 | 4-Cl—$C_6H_4$— | $COOCH_3$ | —$CH_2$—$CH_2$—CN |
| 3.22 | 4-Cl—$C_6H_4$— | $CF_3$ | —$CH_2$—$CH_2$—CN |
| 3.23 | 4-Cl—$C_6H_4$— | CN | —$CH_2$—$CH_2$—CN |
| 3.24 | 2-Cl—4-Cl—$C_6H_3$— | $CF_3$ | —$CH_2$—$CH_2$—CN |
| 3.25 | 2-Cl—4-Cl—$C_6H_3$— | CN | —$CH_2$—$CH_2$—CN |
| 3.26 | 2-Cl—4-Cl—$C_6H_3$— | $COOCH_3$ | —$CH_2$—$CH_2$—CN |
| 3.27 | 2-Cl—3-Cl—$C_6H_3$— | CN | —$CH_2$—$CH_2$—CN |
| 3.28 | 2-Cl—3-Cl—$C_6H_3$— | $CF_3$ | —$CH_2$—$CH_2$—CN |
| 3.29 | 2-Cl—3-Cl—$C_6H_3$ | $COOCH_3$ | —$CH_2$—$CH_2$—CN |
| 3.30 | 2-Cl—3-Cl—$C_6H_3$— | $COOC_2H_5$ | —$CH_2$—$CH_2$—CN |
| 3.31 | 2-Cl—3-Cl—$C_6H_3$— | $COOC_3$—$H_7$—i | —$CH_2$—$CH_2$—CN |
| 3.32 | 2-Cl—3-Cl—$C_6H_3$— | $COOC_3H_7$—n | —$CH_2$—$CH_2$—CN |
| 3.33 | 2-Cl—3-Cl—$C_6H_3$— | $COOC_4H_9$—n | —$CH_2$—$CH_2$—CN |
| 3.34 | 2-Cl—3-Cl—$C_6H_3$— | $COOC_4H_9$—s | —$CH_2$—$CH_2$—CN |
| 3.35 | 2-Cl—3-Cl—$C_6H_3$— | $COOC_4H_9$—i | —$CH_2$—$CH_2$—CN |
| 3.36 | 2-Cl—4-$CF_3$—$C_6H_3$— | $CF_3$ | —$CH_2$—$CH_2$—CN |
| 3.37 | 2-Cl—4-$CF_3$—$C_6H_3$— | CN | —$CH_2$—$CH_2$—CN |
| 3.38 | 2-Cl—4-$CF_3$—$C_6H_3$— | $COOCH_3$ | —$CH_2$—$CH_2$—CN |
| 3.39 | 4-$CH_3$—$C_6H_4$— | $CF_3$ | —$CH_2$—$CH_2$—CN |
| 3.40 | 4-$CH_3$—$C_6H_4$— | CN | —$CH_2$—$CH_2$—CN |
| 3.41 | 4-$CH_3$—$C_6H_4$— | $COOCH_3$ | —$CH_2$—$CH_2$—CN |
| 3.42 | 2-$CF_3$—4-Cl—$C_6H_3$— | CN | —$CH_2$—$CH_2$—CN |
| 3.43 | 2-$CF_3$—4-Cl—$C_6H_3$— | $CF_3$ | —$CH_2$—$CH_2$—CN |
| 3.44 | 2-$CF_3$—4-Cl—$C_6H_3$— | $COOCH_3$ | —$CH_2$—$CH_2$—CN |
| 3.45 | 2-Cl—3-Cl—$C_6H_3$— | CN | —$CH_2$—$CH_2$—$COOCH_3$ |
| 3.46 | 2-Cl—3-Cl—$C_6H_3$— | $CF_3$ | —$CH_2$—$CH_2$—$COOCH_3$ |
| 3.47 | 2-Cl—3-Cl—$C_6H_3$— | $COOCH_3$ | —$CH_2$—$CH_2$—$COOCH_3$ |
| 3.48 | 2-Cl—3-Cl—$C_6H_3$— | $COOC_2H_5$ | —$CH_2$—$CH_2$—$COOCH_3$ |
| 3.49 | 2-Cl—3-Cl—$C_6H_3$— | $COOC_3H_7$—i | —$CH_2$—$CH_2$—$COOCH_3$ |
| 3.50 | 2-Cl—3-Cl—$C_6H_3$— | $COOC_3H_7$—n | —$CH_2$—$CH_2$—$COOCH_3$ |
| 3.51 | 2-Cl—3-Cl—$C_6H_3$— | $COOC_4H_9$—n | —$CH_2$—$CH_2$—$COOCH_3$ |
| 3.52 | 2-Cl—3-Cl—$C_6H_3$— | $COOC_4H_9$—s | —$CH_2$—$CH_2$—$COOCH_3$ |
| 3.53 | 2-Cl—3-Cl—$C_6H_3$— | $COOC_4H_9$—i | —$CH_2$—$CH_2$—$COOCH_3$ |
| 3.54 | 2-Cl—4-$CF_3$—$C_6H_3$— | $CF_3$ | —$CH_2$—$CH_2$—$COOCH_3$ |
| 3.55 | 2-Cl—4-$CF_3$—$C_6H_3$— | CN | —$CH_2$—$CH_2$—$COOCH_3$ |
| 3.56 | 2-Cl—4-$CF_3$—$C_6H_3$— | $COOCH_3$ | —$CH_2$—$CH_2$—$COOCH_3$ |
| 3.57 | 4-$CH_3$—$C_6H_4$— | $CF_3$ | —$CH_2$—$CH_2$—$COOCH_3$ |
| 3.58 | 4-$CH_3$—$C_6H_4$— | CN | —$CH_2$—$CH_2$—$COOCH_3$ |
| 3.59 | 4-$CH_3$—$C_6H_4$— | $COOCH_3$ | —$CH_2$—$CH_2$—$COOCH_3$ |
| 3.60 | 2-$CF_3$—4-Cl—$C_6H_3$— | CN | —$CH_2$—$CH_2$—$COOCH_3$ |
| 3.61 | 2-$CF_3$—4-Cl—$C_6H_3$— | $CF_3$ | —$CH_2$—$CH_2$—$COOCH_3$ |
| 3.62 | 2-CF—4-Cl—$C_6H_3$— | $COOCH_3$ | —$CH_2$—$CH_2$—$COOCH_3$ |
| 3.63 | $C_6H_5$— | $CF_3$ | —$CH_2$—$CH_2$—$COOCH_3$ |
| 3.64 | $C_6H_5$— | $COOCH_3$ | —$CH_2$—$CH_2$—$COOCH_3$ |
| 3.65 | $C_6H_5$— | $COOC_2H_5$ | —$CH_2$—$CH_2$—$COOCH_3$ |
| 3.66 | $C_6H_5$— | CN | —$CH_2$—$CH_2$—$COOCH_3$ |
| 3.67 | 2-Cl—$C_6H_4$— | $CF_3$ | —$CH_2$—$CH_2$—$COOCH_3$ |
| 3.68 | 2-Cl—$C_6H_4$— | $COOC_2H_5$ | —$CH_2$—$CH_2$—$COOCH_3$ |
| 3.69 | 2-Cl—$C_6H_4$— | CN | —$CH_2$—$CH_2$—$COOCH_3$ |
| 3.70 | 2-Cl—$C_6H_4$— | $COOCH_3$ | —$CH_2$—$CH_2$—$COOCH_3$ |
| 3.71 | 2-Cl—$C_6H_4$— | $COOC_3H_7$—i | —$CH_2$—$CH_2$—$COOCH_3$ |

TABLE 3-continued

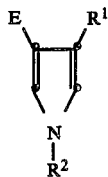

| Comp. No. | E | $R^1$ | $R^2$ |
|---|---|---|---|
| 3.72 | 3-Cl—$C_6H_4$— | $CF_3$ | —$CH_2$—$CH_2$—$COOCH_3$ |
| 3.73 | 3-Cl—$C_6H_4$— | CN | —$CH_2$—$CH_2$—$COOCH_3$ |
| 3.74 | 3-Cl—$C_6H_4$— | $COOC_2H_5$ | —$CH_2$—$CH_2$—$COOCH_3$ |
| 3.75 | 3-Cl—$C_6H_4$— | $COOC_4H_9$—n | —$CH_2$—$CH_2$—$COOCH_3$ |
| 3.76 | 2-F—$C_6H_4$— | $CF_3$ | —$CH_2$—$CH_2$—$COOCH_3$ |
| 3.77 | 2-F—$C_6H_4$— | CN | —$CH_2$—$CH_2$—$COOCH_3$ |
| 3.78 | 2-F—$C_6H_4$— | $COOCH_3$ | —$CH_2$—$CH_2$—$COOCH_3$ |
| 3.79 | 2-$CF_3$—$C_6H_4$— | $COOC_2H_5$ | —$CH_2$—$CH_2$—$COOCH_3$ |
| 3.80 | 2-$CF_3$—$C_6H_4$— | $COOCH_3$ | —$CH_2$—$CH_2$—$COOCH_3$ |
| 3.81 | 2-$CF_3$—$C_6H_4$— | $CF_3$ | —$CH_2$—$CH_2$—$COOCH_3$ |
| 3.82 | 2-$CF_3$—$C_6H_4$— | CN | —$CH_2$—$CH_2$—$COOCH_3$ |
| 3.83 | 4-Cl—$C_6H_4$— | $COOCH_3$ | —$CH_2$—$CH_2$—$COOCH_3$ |
| 3.84 | 4-Cl—$C_6H_4$— | $CF_3$ | —$CH_2$—$CH_2$—$COOCH_3$ |
| 3.85 | 4-Cl—$C_6H_4$ | CN | —$CH_2$—$CH_2$—$COOCH_3$ |
| 3.86 | 2-Cl—4-Cl—$C_6H_3$— | $CF_3$ | —$CH_2$—$CH_2$—$COOCH_3$ |
| 3.87 | 2-Cl—4-Cl—$C_6H_3$— | CN | —$CH_2$—$CH_2$—$COOCH_3$ |
| 3.88 | 2-Cl—4-Cl—$C_6H_3$— | $COOCH_3$ | —$CH_2$—$CH_2$—$COOCH_3$ |
| 3.89 | 2-Br—$C_6H_4$— | | —$CH_2$—$CH_2$—$COOCH_3$ |
| 3.90 | $C_6H_5$— | $CF_3$ | —$CH_2$—$CH_2$—$COOC_2H_5$ |
| 3.91 | $C_6H_5$— | $COOCH_3$ | —$CH_2$—$CH_2$—$COOC_2H_5$ |
| 3.92 | $C_6H_5$— | $COOC_2H_5$ | —$CH_2$—$CH_2$—$COOC_2H_5$ |
| 3.93 | $C_6H_5$— | CN | —$CH_2$—$CH_2$—$COOC_2H_5$ |
| 3.94 | 2-Cl—$C_6H_4$— | $CF_3$ | —$CH_2$—$CH_2$—$COOC_2H_5$ |
| 3.95 | 2-Cl—$C_6H_4$— | $COOC_2H_5$ | —$CH_2$—$CH_2$—$COOC_2H_5$ |
| 3.96 | 2-Cl—$C_6H_4$— | CN | —$CH_2$—$CH_2$—$COOC_2H_5$ |
| 3.97 | 2-Cl—$C_6H_4$— | $COOCH_3$ | —$CH_2$—$CH_2$—$COOC_2H_5$ |
| 3.98 | 2-Cl—$C_6H_4$— | $COOC_3H_7$—i | —$CH_2$—$CH_2$—$COOC_2H_5$ |
| 3.99 | 3-Cl—$C_6H_4$— | $CF_3$ | —$CH_2$—$CH_2$—$COOC_2H_5$ |
| 3.100 | 3-Cl—$C_6H_4$— | CN | —$CH_2$—$CH_2$—$COOC_2H_5$ |
| 3.101 | 3-Cl—$C_6H_4$— | $COOC_2H_5$ | —$CH_2$—$CH_2$—$COOC_2H_5$ |
| 3.102 | 3-Cl—$C_6H_4$— | $COOC_4H_9$—n | —$CH_2$—$CH_2$—$COOC_2H_5$ |
| 3.103 | 2-F—$C_6H_4$— | $CF_3$ | —$CH_2$—$CH_2$—$COOC_2H_5$ |
| 3.104 | 2-F—$C_6H_4$— | CN | —$CH_2$—$CH_2$—$COOC_2H_5$ |
| 3.105 | 2-F—$C_6H_4$— | $COOCH_3$ | —$CH_2$—$CH_2$—$COOC_2H_5$ |
| 3.106 | 2-$CF_3$—$C_6H_4$— | $COOC_2H_5$ | —$CH_2$—$CH_2$—$COOC_2H_5$ |
| 3.107 | 2-$CF_3$—$C_6H_4$— | $COOCH_3$ | —$CH_2$—$CH_2$—$COOC_2H_5$ |
| 3.108 | 2-$CF_3$—$C_6H_4$— | $CF_3$ | —$CH_2$—$CH_2$—$COOC_2H_5$ |
| 3.109 | 2-$CF_3$—$C_6H_4$— | CN | —$CH_2$—$CH_2$—$COOC_2H_5$ |
| 3.110 | 4-Cl—$C_6H_4$— | $COOCH_3$ | —$CH_2$—$CH_2$—$COOC_2H_5$ |
| 3.111 | 4-Cl—$C_6H_4$— | $CF_3$ | —$CH_2$—$CH_2$—$COOC_2H_5$ |
| 3.112 | 4-Cl—$C_6H_4$— | CN | —$CH_2$—$CH_2$—$COOC_2H_5$ |
| 3.113 | 2-Cl—4-Cl—$C_6H_3$— | $CF_3$ | —$CH_2$—$CH_2$—$COOC_2H_5$ |
| 3.114 | 2-Cl—4-Cl—$C_6H_3$— | CN | —$CH_2$—$CH_2$—$COOC_2H_5$ |
| 3.115 | 2-Cl—4-Cl—$C_6H_3$— | $COOCH_3$ | —$CH_2$—$CH_2$—$COOC_2H_5$ |
| 3.116 | 2-Cl—3-Cl—$C_6H_3$— | CN | —$CH_2$—$CH_2$—$COOC_2H_5$ |
| 3.117 | 2-Cl—3-Cl—$C_6H_3$— | $CF_3$ | —$CH_2$—$CH_2$—$COOC_2H_5$ |
| 3.118 | 2-Cl—3-Cl—$C_6H_3$— | $COOCH_3$ | —$CH_2$—$CH_2$—$COOC_2H_5$ |
| 3.119 | 2-Cl—3-Cl—$C_6H_3$— | $COOC_2H_5$ | —$CH_2$—$CH_2$—$COOC_2H_5$ |
| 3.120 | 2-Cl—3-Cl—$C_6H_3$— | $COOC_3H_7$—i | —$CH_2$—$CH_2$—$COOC_2H_5$ |
| 3.121 | 2-Cl—3-Cl—$C_6H_3$— | $COOC_3H_7$—n | —$CH_2$—$CH_2$—$COOC_2H_5$ |
| 3.122 | 2-Cl—3-Cl—$C_6H_3$— | $COOC_4H_9$—n | —$CH_2$—$CH_2$—$COOC_2H_5$ |
| 3.123 | 2-Cl—3-Cl—$C_6H_3$— | $COOC_4H_9$—s | —$CH_2$—$CH_2$—$COOC_2H_5$ |
| 3.124 | 2-Cl—3-Cl—$C_6H_3$— | $COOC_4H_9$—i | —$CH_2$—$CH_2$—$COOC_2H_5$ |
| 3.125 | 2-Cl—4-$CF_3$—$C_6H_3$— | $CF_3$ | —$CH_2$—$CH_2$—$COOC_2H_5$ |
| 3.126 | 2-Cl—4-$CF_3$—$C_6H_3$— | CN | —$CH_2$—$CH_2$—$COOC_2H_5$ |
| 3.127 | 2-Cl—4-$CF_3$—$C_6H_3$— | $COOCH_3$ | —$CH_2$—$CH_2$—$COOC_2H_5$ |
| 3.128 | 4-$CH_3$—$C_6H_4$— | $CF_3$ | —$CH_2$—$CH_2$—$COOC_2H_5$ |
| 3.129 | 4-$CH_3$—$C_6H_4$— | CN | —$CH_2$—$CH_2$—$COOC_2H_5$ |
| 3.130 | 4-$CH_3$—$C_6H_4$— | $COOCH_3$ | —$CH_2$—$CH_2$—$COOC_2H_5$ |
| 3.131 | 2-$CF_3$—4-Cl—$C_6H_3$— | CN | —$CH_2$—$CH_2$—$COOC_2H_5$ |
| 3.132 | 2-$CF_3$—4-Cl—$C_6H_3$— | $CF_3$ | —$CH_2$—$CH_2$—$COOC_2H_5$ |
| 3.133 | 2-$CF_3$—4-Cl—$C_6H_3$— | $COOCH_3$ | —$CH_2$—$CH_2$—$COOC_2H_5$ |
| 3.134 | 2-Cl—3-Cl—$C_6H_3$— | CN | —$CH_2$—$CH_2$—$COOC_3H_7$—n |
| 3.135 | 2-Cl—3-Cl—$C_6H_3$— | $CF_3$ | —$CH_2$—$CH_2$—$COOC_3H_7$—n |
| 3.136 | 2-Cl—3-Cl—$C_6H_3$— | $COOCH_3$ | —$CH_2$—$CH_2$—$COOC_3H_7$—n |
| 3.137 | 2-Cl—3-Cl—$C_6H_3$— | $COOC_2H_5$ | —$CH_2$—$CH_2$—$COOC_3H_7$—n |
| 3.138 | 2-Cl—3-Cl—$C_6H_3$— | $COOC_3H_7$—i | —$CH_2$—$CH_2$—$COOC_3H_7$—n |
| 3.139 | 2-Cl—3-Cl—$C_6H_3$— | $COOC_3H_7$—n | —$CH_2$—$CH_2$—$COOC_3H_7$—n |
| 3.140 | 2-Cl—3-Cl—$C_6H_3$— | $COOC_4H_9$—n | —$CH_2$—$CH_2$—$COOC_3H_7$—n |
| 3.141 | 2-Cl—3-Cl—$C_6H_3$— | $COOC_4H_9$—s | —$CH_2$—$CH_2$—$COOC_3H_7$—n |
| 3.142 | 2-Cl—3-Cl—$C_6H_3$— | $COOC_4H_9$—i | —$CH_2$—$CH_2$—$COOC_3H_7$—n |

TABLE 3-continued

E—[pyrrole ring]—R¹, N—R²

| Comp. No. | E | R¹ | R² |
|---|---|---|---|
| 3.143 | 2-Cl—4-CF$_3$—C$_6$H$_3$— | CF$_3$ | —CH$_2$—CH$_2$—COOC$_3$H$_7$—n |
| 3.144 | 2-Cl—4-CF$_3$—C$_6$H$_3$— | CN | —CH$_2$—CH$_2$—COOC$_3$H$_7$—n |
| 3.145 | 2-Cl—4-CF$_3$—C$_6$H$_3$— | COOCH$_3$ | —CH$_2$—CH$_2$—COOC$_3$H$_7$—n |
| 3.146 | 4-CH$_3$—C$_6$H$_4$— | CF$_3$ | —CH$_2$—CH$_2$—COOC$_3$H$_7$—n |
| 3.147 | 4-CH$_3$—C$_6$H$_4$— | CN | —CH$_2$—CH$_2$—COOC$_3$H$_7$—n |
| 3.148 | 4-CH$_3$—C$_6$H$_4$— | COOCH$_3$ | —CH$_2$—CH$_2$—COOC$_3$H$_7$—n |
| 3.149 | 2-CF$_3$—4-Cl—C$_6$H$_3$— | CN | —CH$_2$—CH$_2$—COOC$_3$H$_7$—n |
| 3.150 | 2-CF$_3$—4-Cl—C$_6$H$_3$— | CF$_3$ | —CH$_2$—CH$_2$—COOC$_3$H$_7$—n |
| 3.151 | 2-CF$_3$—4-Cl—C$_6$H$_3$— | COOCH$_3$ | —CH$_2$—CH$_2$—COOC$_3$H$_7$—n |
| 3.152 | C$_6$H$_5$— | CF$_3$ | —CH$_2$—CH$_2$—COOC$_3$H$_7$—n |
| 3.153 | C$_6$H$_5$— | COOCH$_3$ | —CH$_2$—CH$_2$—COOC$_3$H$_7$—n |
| 3.154 | C$_6$H$_5$— | COOC$_2$H$_5$ | —CH$_2$—CH$_2$—COOC$_3$H$_7$—n |
| 3.155 | C$_6$H$_5$— | CN | —CH$_2$—CH$_2$—COOC$_3$H$_7$—n |
| 3.156 | 2-Cl—C$_6$H$_4$— | CF$_3$ | —CH$_2$—CH$_2$—COOC$_3$H$_7$—n |
| 3.157 | 2-Cl—C$_6$H$_4$— | COOC$_2$H$_5$ | —CH$_2$—CH$_2$—COOC$_3$H$_7$—n |
| 3.158 | 2-Cl—C$_6$H$_4$— | CN | —CH$_2$—CH$_2$—COOC$_3$H$_7$—n |
| 3.159 | 2-Cl—C$_6$H$_4$— | COOCH$_3$ | —CH$_2$—CH$_2$—COOC$_3$H$_7$—n |
| 3.160 | 2-Cl—C$_6$H$_4$— | COOC$_3$H$_7$—i | —CH$_2$—CH$_2$—COOC$_3$H$_7$—n |
| 3.161 | 3-Cl—C$_6$H$_4$— | CF$_3$ | —CH$_2$—CH$_2$—COOC$_3$H$_7$—n |
| 3.162 | 3-Cl—C$_6$H$_4$— | CN | —CH$_2$—CH$_2$—COOC$_3$H$_7$—n |
| 3.163 | 3-Cl—C$_6$H$_4$— | COOC$_2$H$_5$ | —CH$_2$—CH$_2$—COOC$_3$H$_7$—n |
| 3.164 | 3-Cl—C$_6$H$_4$— | COOC$_4$H$_9$—n | —CH$_2$—CH$_2$—COOC$_3$H$_7$—n |
| 3.165 | 2-F—C$_6$H$_4$— | CF$_3$ | —CH$_2$—CH$_2$—COOC$_3$H$_7$—n |
| 3.166 | 2-F—C$_6$H$_4$— | CN | —CH$_2$—CH$_2$—COOC$_3$H$_7$—n |
| 3.167 | 2-F—C$_6$H$_4$— | COOCH$_3$ | —CH$_2$—CH$_2$—COOC$_3$H$_7$—n |
| 3.168 | 2-CF$_3$—C$_6$H$_4$— | COOC$_2$H$_5$ | —CH$_2$—CH$_2$—COOC$_3$H$_7$—n |
| 3.169 | 2-CF$_3$—C$_6$H$_4$— | COOCH$_3$ | —CH$_2$—CH$_2$—COOC$_3$H$_7$—n |
| 3.170 | 2-CF$_3$—C$_6$H$_4$— | CF$_3$ | —CH$_2$—CH$_2$—COOC$_3$H$_7$—n |
| 3.171 | 2-CF$_3$—C$_6$H$_4$— | CN | —CH$_2$—CH$_2$—COOC$_3$H$_7$—n |
| 3.172 | 4-Cl—C$_6$H$_4$— | COOCH$_3$ | —CH$_2$—CH$_2$—COOC$_3$H$_7$—n |
| 3.173 | 4-Cl—C$_6$H$_4$— | CF$_3$ | —CH$_2$—CH$_2$—COOC$_3$H$_7$—n |
| 3.174 | 4-Cl—C$_6$H$_4$— | CN | —CH$_2$—CH$_2$—COOC$_3$H$_7$—n |
| 3.175 | 2-Cl—4-Cl—C$_6$H$_3$— | CF$_3$ | —CH$_2$—CH$_2$—COOC$_3$H$_7$—n |
| 3.176 | 2-Cl—4-Cl—C$_6$H— | CN | —CH$_2$—CH$_2$—COOC$_3$H$_7$—n |
| 3.177 | 2-Cl—4-Cl—C$_6$H$_3$— | COOCH$_3$ | —CH$_2$—CH$_2$—COOC$_3$H$_7$—n |
| 3.178 | 2-Cl—3-Cl—C$_6$H$_3$— | CN | —CH=CH$_2$ |
| 3.179 | 2-Cl—3-Cl—C$_6$H$_3$— | CF$_3$ | —CH=CH$_2$ |
| 3.180 | 2-Cl—3-Cl—C$_6$H$_3$— | CN | —CH$_2$CH$_2$—Cl |
| 3.181 | 2-Cl—3-Cl—C$_6$H$_3$— | CF$_3$ | —CH$_2$—CH$_2$—Cl |
| 3.182 | 2-Cl—3-Cl—C$_6$H$_3$— | CF$_3$ | —CH$_2$—CH$_2$—SO$_2$—C$_6$H$_4$—CH$_3$ |
| 3.183 | 2-Cl—3-Cl—C$_6$H$_3$— | CN | —CH$_2$—CH$_2$—SO$_2$—C$_6$H$_4$—CH$_3$ |

TABLE 4

E—CH=CCl—CF$_3$

| Comp.No. | E |
|---|---|
| 4.1 | C$_6$H$_5$— |
| 4.2 | 2-Cl—C$_6$H$_4$— |
| 4.3 | 3-Cl—C$_6$H$_4$— |
| 4.4 | 4-Cl—C$_6$H$_4$— |
| 4.5 | 2-F—C$_6$H$_4$— |
| 4.6 | 2-Br—C$_6$H$_4$— |
| 4.7 | 2-CF3—C$_6$H$_4$— |
| 4.8 | 2-CF—4-Cl—C$_6$H$_3$— |
| 4.9 | 2-Cl—4-Cl—C$_6$H$_3$— |
| 4.10 | 2-Cl—3-Cl—C$_6$H$_3$— |
| 4.11 | 2-Cl—4-CF$_3$—C$_6$H$_3$— |
| 4.12 | 4-CH$_3$—C$_6$H$_4$— |

TABLE 5

E—CH(OH)—CCl$_2$—CF$_3$

| Comp. No. | E |
|---|---|
| 5.1 | C$_6$H$_5$— |
| 5.2 | 2-Cl—C$_6$H$_4$— |

TABLE 5-continued $$\text{E}-\text{CH}-\text{CCl}_2-\text{CF}_3$$
$$|$$
$$\text{OH}$$

| Comp. No. | E |
|---|---|
| 5.3 | 3-Cl—C$_6$H$_4$— |
| 5.4 | 4-Cl—C$_6$H$_4$— |
| 5.5 | 2-F—C$_6$H$_4$— |
| 5.6 | 2-Br—C$_6$H$_4$— |
| 5.7 | 2-CF$_3$—C$_6$H$_4$— |
| 5.8 | 2-CF$_3$—4-Cl—C$_6$H$_3$— |
| 5.9 | 2-Cl—4-Cl—C$_6$H$_3$— |
| 5.10 | 2-Cl—3-Cl—C$_6$H$_3$— |
| 5.11 | 2-Cl—4-CF$_3$—C$_6$H$_3$— |
| 5.12 | 4-CH$_3$—C$_6$H$_4$— |

TABLE 6

$$\text{E}-\text{CH}-\text{CCl}_2-\text{CF}_3$$
$$|$$
$$\text{O}-\text{COCH}_3$$

| Comp. No. | E |
|---|---|
| 6.1 | C$_6$H$_5$— |
| 6.2 | 2-Cl—C$_6$H$_4$— |
| 6.3 | 3-Cl—C$_6$H$_4$— |
| 6.4 | 4-Cl—C$_6$H$_4$— |
| 6.5 | 2-F—C$_6$H$_4$— |
| 6.6 | 2-Br—C$_6$H$_4$— |
| 6.7 | 2-CF$_3$—C$_6$H$_4$— |
| 6.8 | 2-CF$_3$—4-Cl—C$_6$H$_3$— |
| 6.9 | 2-Cl—4-Cl—C$_6$H$_3$— |
| 6.10 | 2-Cl—3-Cl—C$_6$H$_3$— |
| 6.11 | 2-Cl—4-CF$_3$—C$_6$H$_3$— |
| 6.12 | 4-CH$_3$—C$_6$H$_4$— |

Formulation Examples for liquid active ingredients of the formula I (%=percent by weight)

| F1. Emulsion concentrates | (a) | (b) | (c) |
|---|---|---|---|
| active ingredient from Table 3 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| F2. Solutions | (a) | (b) | (c) | (d) |
|---|---|---|---|---|
| active ingredient from Table 3 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

(M.W. = molecular weight)

The solutions are suitable for application in the form of very fine drops.

| F3. Granulates | (a) | (b) |
|---|---|---|
| active ingredient from Table 3 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F4. Dusts | (a) | (b) |
|---|---|---|
| active ingredient from Table 3 | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation Examples for solid active ingredients of the formula I (%=percent by weight)

| F5. Wettable powders | (a) | (b) | (c) |
|---|---|---|---|
| active ingredient from Table 3 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives, and the mixture is thoroughly ground in a suitable mill. Wettable powders which can be diluted with water to give suspensions of the required concentration are obtained.

| F6. Emulsion concentrate | |
|---|---|
| active ingredient from Table 3 | 10% |
| octylphenol polyethylene glycol ether (4–5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of the required concentration can be obtained from this concentrate by dilution with water.

| F7. Dusts | (a) | (b) |
|---|---|---|
| active ingredient from Table 3 | 5% | 8% |
| talcum | 95% | — |
| kaolin | — | 92% |

Dusts ready for use are obtained by mixing the active ingredient with the carriers and grinding the mixture in a suitable mill.

| F8. Extruder granulate | |
|---|---|
| active ingredient from Table 3 | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

| F9. Coated granulate | |
|---|---|
| active ingredient from Table 3 | 3% |
| polyethylene glycol (M.W. 200) | 3% |
| kaolin | 94% |

(M.W. = molecular weight)

The finely ground active ingredient is evenly applied in a mixer to the kaolin moistened with polyethylene glycol. Dustfree coated granules are obtained in this manner.

| F.10. Suspension concentrate | |
|---|---|
| active ingredient from Table 3 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

BIOLOGICAL EXAMPLES

Example B1.

Action against *Botrytis cinerea* on beans

Residual-protective action

Bean plants about 10 cm in height are sprayed with a spray liquor prepared from wettable powder of the active ingredient (0.02% of active ingredient). The plants are infested after 48 hours with a conidiospore suspension of the fungus. The extent of fungus infection is assessed after incubation of the infested plants for 3 days at 21° C. with 95-100% relative humidity.

The compounds from Table 3 greatly reduce fungus infection not only in the above model test but also in the field test. At a concentration of 0.02%, compounds from for example Table 3 prove fully effective (infection 0 to 5%). Infection on untreated but infested bean plants is 100%.

Example B2:

Action against *Botrytis cinerea* on apples

Artificially damaged apples are treated by applying drops of spray liquor, prepared from wettable powder of the active substance, to the damaged areas on the apples. The treated fruit is then inoculated with a spore suspension of *Botrytis cinerea*, and is incubated for one week at about 20° C. with high relative humidity.

For an assessment of the results, the decayed areas of damage are counted, and from the number is deduced the fungicidal action of the test substance. Amongst other effective compounds tested, the compounds from Table 3 completely prevent fungus infection, whereas the level of infection on untreated control fruit is 100%.

What is claimed is:

1. A 3-phenylpyrrole compound of formula I

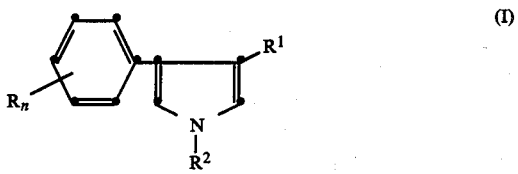

wherein $R^1$ is cyano, trifluoromethyl or $C_1$-$C_4$-alkoxycarbonyl, $R^2$ is 2-ethoxycarbonylethyl or 2-cyanoethyl, R is halogen, $C_1$-$C_4$-alkyl or $C_1$-$C_4$-haloalkyl, and n is zero, one or two.

2. A compound according to claim 1, wherein the phenyl group is substituted in the 2- and 3-position by two chlorine atoms.

3. A compound according to claim 1, wherein $R^1$ is cyano or trifluoromethyl.

4. A process for controlling phytopathogenic microorganisms, which process comprises applying to the plants or to the locus thereof an effective amount of a 3-phenylpyrrole compound of the formula I according to claim 2.

5. A compound according to claim 1, wherein the phenyl group is substituted in the 2- and/or 3-position by chlorine atoms, $R^1$ is trifluoromethyl or cyano, and $R^2$ is ethoxycarbonylethyl or 2-cyanoethyl.

6. 1-Ethoxycarbonylethyl-3-(2,3-dichlorophenyl)-4-trifluoromethylpyrrole according to claim 1.

7. 1-Ethoxycarbonylethyl-4-cyano-3-(2,3-dichlorophenyl)pyrrole according to claim 1.

8. A phytomicrobicidal composition, which contains as active ingredient an effective amount of a compound of the formula I according to claim 1, together with carriers and/or other additives.

9. A method of controlling phytopathogenic microorganisms, which method comprises applying to cultivated plants, to parts of plants or to the locus thereof a microbicidally effective amount of a compound of formula I according to claim 1.

10. A process according to claim 4, wherein the microorganisms concerned are phytopathogenic fungi.

11. A process according to claim 4, wherein the microorganisms concerned are fungi of the Fungi imperfecti family, particularly *Botrytis*.

* * * * *